United States Patent
Miyawaki et al.

(10) Patent No.: US 8,865,886 B2
(45) Date of Patent: Oct. 21, 2014

(54) METHOD FOR RECOVERY/REUSE OF N-OXYL COMPOUND

(75) Inventors: Shoichi Miyawaki, Tokyo (JP); Shiho Katsukawa, Tokyo (JP); Hiroshi Abe, Tokyo (JP); Yuko Iijima, Tokyo (JP); Akira Isogai, Tokyo (JP)

(73) Assignee: Nippon Paper Industries Co., Ltd., Tokyo (JP)

( * ) Notice: Subject to any disclaimer, the term of this patent is extended or adjusted under 35 U.S.C. 154(b) by 474 days.

(21) Appl. No.: 13/257,732

(22) PCT Filed: Feb. 16, 2010

(86) PCT No.: PCT/JP2010/052277
§ 371 (c)(1),
(2), (4) Date: Sep. 20, 2011

(87) PCT Pub. No.: WO2010/116794
PCT Pub. Date: Oct. 14, 2010

(65) Prior Publication Data
US 2012/0065389 A1 Mar. 15, 2012

(30) Foreign Application Priority Data
Mar. 30, 2009 (JP) ................................. 2009-082296

(51) Int. Cl.
| | | |
|---|---|---|
| C07D 211/00 | (2006.01) | |
| C08B 16/00 | (2006.01) | |
| B01D 61/00 | (2006.01) | |
| B01D 61/42 | (2006.01) | |
| C07D 211/94 | (2006.01) | |
| B01J 31/02 | (2006.01) | |
| B01J 31/40 | (2006.01) | |
| C08B 15/02 | (2006.01) | |

(52) U.S. Cl.
CPC ........... *C07D 211/94* (2013.01); *B01J 31/0235* (2013.01); *B01J 31/40* (2013.01); *C08B 15/02* (2013.01); *B01J 2231/70* (2013.01)

USPC .............. 536/57; 204/536; 204/544; 546/184

(58) Field of Classification Search
CPC .... C08B 16/00; C07D 295/023; B01D 57/02; B01J 47/08
USPC ....................... 536/57; 204/536, 544; 546/184
See application file for complete search history.

(56) References Cited

U.S. PATENT DOCUMENTS

| | | |
|---|---|---|
| 6,335,464 B1 | 1/2002 | Ochi et al. |
| 2007/0208204 A1 * | 9/2007 | Meyer et al. ..................... 585/4 |

FOREIGN PATENT DOCUMENTS

| | | |
|---|---|---|
| EP | 1 027 931 A1 | 8/2000 |
| JP | 2009-242590 | 10/2009 |

OTHER PUBLICATIONS

Greiter et al Journal of Membrane Science 2004, 233, 11-19.*
Supplementary European Search Report in EP 10 76 1496 dated Aug. 27, 2012.
Saito et al, "Cellulose Nanofibers Prepared by TEMPO-Mediated Oxidation of Native Cellulose", Biomacromolecules, vol. 8, No. 8, Jan. 1, 2007, pp. 2485-2491, XP008133674.
International Search Report for PCT/JP2010/052277, mailed May 25, 2010.

* cited by examiner

*Primary Examiner* — John Mabry
(74) *Attorney, Agent, or Firm* — Nixon & Vanderhye P.C.

(57) ABSTRACT

An effluent produced in oxidation of a cellulosic material with an oxidizing agent in the presence of an N-oxyl compound and a bromide and/or iodide is deionized by electrodialysis to an inorganic salt concentration of less than 0.4%, whereby the N-oxyl compound in the effluent is concentrated and recovered. The N-oxyl compound thus recovered can be reused in oxidation of a cellulosic material. Preferably, the effluent is subjected to reduction treatment and ion exchange resin treatment prior to the electrodialysis.

5 Claims, No Drawings

METHOD FOR RECOVERY/REUSE OF N-OXYL COMPOUND

This application is the U.S. national phase of International Application No. PCT/JP2010/052277 filed 16 Feb. 2010 which designated the U.S. and claims priority to JP Patent Application No. 2009-082296 filed 30 Mar. 2009, the entire contents of each of which are hereby incorporated by reference.

TECHNICAL FIELD

The present invention relates to a method of efficiently recovering an expensive N-oxyl compound from an effluent produced in a process of producing oxidized cellulose using the N-oxyl compound as a cellulose oxidation catalyst, and reusing the effluent containing the N-oxyl compound after the recovery.

BACKGROUND ART

It is known that by treating a cellulosic material in the presence of a catalytic amount of an N-oxyl compound and a chlorine based oxidizing agent, primary hydroxyl groups of cellulose can be oxidized into carboxyl groups and aldehyde groups (Non-patent Document 1).

The N-oxyl compound used as a catalyst in the above oxidized cellulose production technique is very expensive. Thus, it is desired to recover the N-oxyl compound from the effluent after completion of the reaction and then reuse the recovered N-oxyl compound. However, there has not been reported any method of recovering an N-oxyl compound from an effluent and reusing the N-oxyl compound thus recovered.

CITATION LIST

Non-Patent Document

Non-patent Document: Saito, T., et al., Cellulose Commun., 14 (2), 62 (2007)

SUMMARY OF INVENTION

Technical Problem

Common methods for the recovery of a low-molecular-weight organocatalyst which is amphipathic, i.e., soluble in both water and an organic solvent, and has low volatility, such as an N-oxyl compound, are extraction, adsorption and the like. However, in liquid-liquid extraction with an organic solvent such as hexane, the solvent remains in an effluent after extraction. Thus, there is environmental concern. Furthermore, an additional step of recovering the organic solvent is necessary, which requires additional cost. Further, in a method of selectively adsorbing and recovering a catalyst using a hydrophobic synthetic resin or the like, an organic solvent is used in desorption of the catalyst adsorbed on the resin surface. Thus, like the liquid-liquid extraction described above, there is environmental concern and, furthermore, additional cost is needed.

In view of the foregoing, the present invention is aimed at providing a method of recovering N-oxyl compounds at a high recovery rate from an effluent after oxidation of a cellulosic material which contains inorganic salts, water-soluble organic substances, N-oxyl compounds and the like.

Solution to Problem

As a result of extensive and intensive studies, the present inventors found that by subjecting an effluent after oxidation of a cellulosic material to electrodialysis to deionize the effluent to a particular inorganic salt concentration, an N-oxyl compound could be recovered easily at a high recovery rate and, furthermore, the N-oxyl compound thus recovered could be reused suitably. By this finding, the present invention was completed. Specifically, the present invention is as follows.

1. A method of recovering an N-oxyl compound from an effluent which is produced in oxidation of a cellulosic material with an oxidizing agent in the presence of (1) an N-oxyl compound and (2) a compound selected from the group consisting of a bromide, an iodide and a mixture thereof, comprising subjecting the effluent to deionization by electrodialysis such that the resulting effluent has an inorganic salt concentration of less than 0.4%.
2. The method of 1, wherein the effluent is subjected to ion exchange resin treatment prior to the deionization by electrodialysis.
3. The method of 1 or 2, wherein the effluent is subjected to reduction treatment prior to the deionization by electrodialysis.
4. The method of any one of 1 to 3, wherein the effluent is subjected to reduction treatment and then ion exchange resin treatment and thereafter deionization by electrodialysis.
5. The method of any one of 1 to 4, wherein the N-oxyl compound which is recovered is 2,2,6,6-tetramethyl-1-piperidin-N-oxyradical (TEMPO), 4-hydroxy-2,2,6,6-tetramethyl-1-piperidin-N-oxyradical (4-hydroxy TEMPO), a 4-hydroxy TEMPO derivative obtained by etherification or esterification of a hydroxyl group of 4-hydroxy TEMPO, an aza-adamantane type nitroxy radical, or a mixture thereof.
6. A method of reusing an N-oxyl compound, comprising using an N-oxyl compound which is recovered by the method of any one of 1 to 5 in an oxidation reaction of a cellulosic material with an oxidizing agent in the presence of (1) an N-oxyl compound and (2) a compound selected from the group consisting of a bromide, an iodide and a mixture thereof, wherein the N-oxyl compound which is recovered by the method of any one of 1 to 5 is used as all or part of the N-oxyl compound which is used in the oxidation reaction.
7. A method of producing a cellulose nanofiber dispersion, comprising: preparing an oxidized cellulosic material using an N-oxyl compound which is recovered by the method of any one of Claims 1 to 5 in an oxidation reaction of a cellulosic material with an oxidizing agent in the presence of (1) an N-oxyl compound and (2) a compound selected from the group consisting of a bromide, an iodide and a mixture thereof, wherein the N-oxyl compound which is recovered by the method of any one of Claims 1 to 5 is used as all or part of the N-oxyl compound which is used in the oxidation reaction; and subjecting the oxidized cellulosic material to wet mechanical disintegration treatment to prepare a cellulose nanofiber dispersion.

Advantageous Effects of Invention

In the present invention, an effluent containing an N-oxyl compound is deionized by electrodialysis, whereby the expensive N-oxyl compound is recovered at a high recovery rate of preferably 80% or higher and, at the same time, the resulting effluent has an inorganic salt concentration of less than 0.4%. By simultaneously achieving such a high catalyst recovery rate and a high deionization rate, the treated liquid in which the N-oxyl compound is concentrated can be reused as all or part of an oxidation catalyst in oxidation of a cellulosic material, whereby production costs of oxidized pulp can be reduced.

An electrodialytic membrane has been used for deionization of an aqueous liquid, but the present application was the first to find that an N-oxyl compound could be recovered at a high recovery rate by electrodialysis from an effluent produced by oxidation of a cellulosic material. Since an N-oxyl compound used in oxidation of a cellulosic material has a relatively small molecular weight, it was predicted that in electrodialysis, the N-oxyl compound would pass through a membrane and diffuse in large amount and most of the N-oxyl compound would be lost together with inorganic salts and the like. Hence, it was a surprising result that the N-oxyl compound could be recovered at a high recovery rate by the electrodialysis of the present invention.

Further, the present inventors found for the first time that when a liquid after electrodialysis which contained an N-oxyl compound and was deionized to an inorganic salt concentration of less than 0.4% was reused as all or part of an oxidation catalyst in oxidation of a cellulosic material, cellulose nanofibers with high transparency could be obtained.

Furthermore, in the present invention, the effluent may be subjected to ion exchange resin treatment prior to the electrodialysis to remove impurities (substances other than N-oxyl compound) contained in the effluent, whereby deionization efficiency in the electrodialysis can be improved and the N-oxyl compound can be recovered at a high recovery rate. The resulting liquid containing the N-oxyl compound can be reused as all or part of an oxidation catalyst in oxidation of a cellulosic material, and cellulose nanofibers with even higher transparency can be obtained.

DESCRIPTION OF EMBODIMENTS

The present invention is a method of recovering an N-oxyl compound from an effluent which is produced by oxidation of a cellulosic material using the N-oxyl compound, and reusing the recovered N-oxyl compound, comprising deionizing by electrodialysis an effluent containing as impurities a bromide and/or iodide, sodium chloride, oxidizing agent, calcium ions, water-soluble polysaccharides derived from pulp and the like as well as the N-oxyl compound, whereby the impurities are removed from the effluent and the N-oxyl compound is concentrated in the effluent.

(Oxidation of Cellulosic Material Using N-Oxyl Compound)

As the effluent to be subjected to the electrodialysis in the present invention, an effluent which is produced by oxidation reaction of a cellulosic material with an oxidizing agent in the presence of an N-oxyl compound and a bromide and/or iodide can be used.

Examples of an N-oxyl compound which is used in the oxidation of a cellulosic material and can be recovered by the present invention include a substance represented by the following general formula (Formula 1):

[Formula 1]

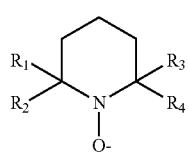

Formula 1 wherein $R_1$ to $R_4$ represent the same or different alkyl groups having about 1 to 4 carbon atoms.

Among the compounds represented by Formula 1, 2,2,6,6-tetramethyl-1-piperidin-oxyradical (hereinafter "TEMPO") and 4-hydroxy-2,2,6,6-tetramethyl-1-piperidin-oxyradical (hereinafter "4-hydroxy TEMPO") are preferred. A 4-hydroxy TEMPO derivative represented by any one of Formulas 2 to 4 below, to which adequate hydrophobicity is imparted by etherification of hydroxyl groups of 4-hydroxy TEMPO with alcohol or by esterification of hydroxyl groups of 4-hydroxy TEMPO with carboxylic acid or sulfonic acid, is inexpensive, and uniform oxidized pulp can be obtained from such a 4-hydroxy TEMPO derivative. Thus, the 4-hydroxy TEMPO derivative can be used suitably in the oxidation of a cellulosic material and, furthermore, can be recovered efficiently by the method of the present invention.

[Formula 2]

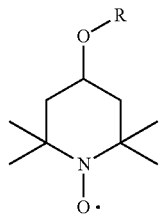

Formula 2

[Formula 3]

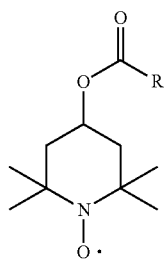

Formula 3

[Formula 4]

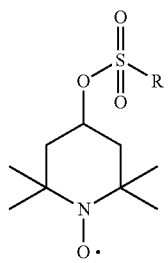

Formula 4

In Formulas 2 to 4, R represents a straight or branched carbon chain having not more than 4 carbon atoms.

An N-oxyl compound represented by Formula 5 below, i.e., aza-adamantane type nitroxy radical, is also preferred for the same reason as the 4-hydroxy TEMPO derivative.

[Formula 5]

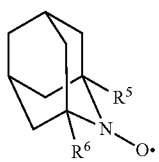

Formula 5

In Formula 5, $R^5$ and $R^6$ represent the same or different hydrogen atoms or the same or different $C_1$ to $C_6$ straight or branched alkyl groups.

In general, the amount of N-oxyl compound used in the oxidation of a cellulosic material is about 0.01 to 10 mmol, preferably about 0.01 to 1 mmol, more preferably about 0.05 to 0.5 mmol, based on 1 g (absolute dry weight) of the cellulosic material.

Examples of a bromide or iodide used in the oxidation of a cellulosic material include compounds which can be dissociated in water and ionized, such as an alkali metal bromide and an alkali metal iodide. In general, a bromide or iodide is used in an amount of about 0.1 to 100 mmol, preferably about 0.1 to 10 mmol, more preferably about 0.5 to 5 mmol, based on 1 g (absolute dry weight) of the cellulosic material.

Examples of an oxidizing agent used in the oxidation of a cellulosic material include a halogen, hypohalogenous acid, halogenous acid, perhalogenic acid or a salt, halogen oxide or peroxide thereof, etc. Among these oxidizing agents, use of sodium hypochlorite which is inexpensive and has less environmental load is especially preferred in terms of production costs. In general, an oxidizing agent is used in an amount of about 0.5 to 500 mmol, preferably about 0.5 to 50 mmol, more preferably about 2.5 to 25 mmol, based on 1 g (absolute dry mass) of the cellulosic material.

The cellulosic material which is oxidized with an oxidizing agent in the presence of an N-oxyl compound and a bromide and/or iodide is not particularly limited, and kraft pulp or sulfite pulp of various wood origins, powdery cellulose formed by pulverizing such pulp by a high pressure homogenizer, a mill or the like, or a microcrystalline cellulose powder formed by purifying such a material by chemical treatment such as acid hydrolysis is used. Plants such as kenaf, hemp, rice, bagasse and bamboo are also used. Among these cellulosic materials, use of bleached kraft pulp, bleached sulfite pulp, powdery cellulose, or microcrystalline cellulose powder is preferred in terms of mass production and costs.

In general, the oxidation of a cellulosic material with an oxidizing agent in the presence of an N-oxyl compound and a bromide and/or iodide is conducted at room temperature, about 15 to 30° C., for a reaction time of about 0.5 to 4 hours with addition of an alkaline solution such as an aqueous solution of sodium hydroxide to maintain the pH of the reaction liquid at about 9 to 12, preferably about 10 to 11.

The amount of carboxyl groups in the resulting oxidized pulp is calculated as follows. Sixty milliliters of 0.5% by mass slurry of oxidized pulp is prepared, and an aqueous solution of 0.1 M hydrochloric acid is added to give a pH of 2.5. Then, an aqueous solution of 0.05 N sodium hydroxide is dropped, and the conductivity is measured until the pH reaches pH 11. From the amount of sodium hydroxide (a) consumed during a weakly acidic neutralization phase in which a change in the conductivity is gradual, the amount of carboxyl groups can be calculated by the following formula:

Amount of carboxyl groups [mmol/g pulp]=a [ml]× 0.05/mass of oxidized pulp [g].

(Effluent Produced in Oxidation of Cellulosic Material)

In the present invention, an N-oxyl compound is recovered from the effluent which is produced when a cellulosic material is oxidized with an oxidizing agent in the presence of the N-oxyl compound and a bromide and/or iodide. The effluent can be obtained by removing an oxidized cellulosic material by, for example, filtration of the reaction liquid after completion of the oxidation reaction of the cellulosic material.

It is considered that the effluent which is produced when a cellulosic material is oxidized with an oxidizing agent in the presence of an N-oxyl compound and a bromide and/or iodide contains impurities such as the bromide and/or iodide, sodium chloride, the oxidizing agent, water-soluble anionic oligomers or copolymers (water-soluble polysaccharides) derived from cellulose and hemicellulose, and calcium ions, as well as the N-oxyl compound.

(Electrodialysis of Effluent)

Electrodialysis is a method of separating ionic substances contained in a liquid by use of ion exchange membranes and electricity. In the electrodialysis of the present invention, a commonly-used cation exchange membrane and a commonly-used anion exchange membrane are used to separate cations and anions in the liquid, whereby the concentration of inorganic salts in the effluent is reduced to less than 0.4%. As the cation exchange membrane, for example, various cation exchange membranes in which acidic ion exchange groups such as sulfonic acid groups, sulfuric acid ester groups, phosphoric acid ester groups and carboxyl groups are introduced in styrene-divinylbenzene copolymers can be used. As the anion exchange membrane, for example, various anion exchange membranes in which basic ion exchange groups such as dodecylamino groups, dioctylamino groups and pyridyl groups are introduced in styrene-divinylbenzene copolymers can be used.

In the present invention, an effluent containing an N-oxyl compound which is produced by the oxidation of a cellulosic material is passed through an electrodialyzer equipped with the above commonly-used ion exchange membranes, whereby the effluent is electrodialyzed and deionized such that the resulting effluent has an inorganic salt concentration of less than 0.4%. The voltage applied to the electrodialyzer, the current density and the treatment time can be selected as appropriate according to the concentration of inorganic slats to be deionized, but in order to reduce the concentration of inorganic salts in the effluent to less than 0.4%, it is desirable to set the conditions such that the deionization rate of the electrodialysis is 20% or higher, preferably 30% or higher. Specifically, it is preferable to conduct the electrodialysis at a voltage of 5 V to 15 V for 2 to 60 minutes, preferably 10 to 30 minutes, and to use an aqueous solution of 3 to 5% sulfate, an aqueous solution of 3 to 5% nitrate or the like as an electrode solution.

The effluent deionized by the electrodialysis of the present invention contains the N-oxyl compound at relatively high concentration. The rate of recovery of N-oxyl compound by the electrodialysis of the present invention is 80% or higher, preferably 85% or higher, most preferably 90% or higher. By recovering and reusing the expensive N-oxyl compound, the production cost of oxidized pulp can be reduced, because the amount of new N-oxyl compound used can be reduced.

(Reuse of N-Oxyl Compound)

The effluent containing the N-oxyl compound which is obtained by the electrodialysis of the present invention has a low concentration of impurities such as inorganic salts and macromolecular substances, and contains at relatively high concentration of the N-oxyl compound having oxidation catalytic activity. Thus, the effluent can be reused directly as all or part of an oxidation catalyst in the oxidation of a cellulosic material without any further treatment of the N-oxyl compound such as purification/extraction, and oxidized pulp can be produced at high efficiency as in the case of using a fresh oxidation catalyst (N-oxyl compound).

(Treatment with Ion Exchange Resin)

In the present invention, the effluent may be subjected to ion exchange resin treatment prior to the electrodialysis of the effluent. By subjecting the effluent to ion exchange resin treatment prior to the electrodialysis, the deionization efficiency in the electrodialysis can be improved so that the N-oxyl compound can be recovered at a higher recovery rate. Further, the liquid containing the N-oxyl compound recovered by conducting both the ion exchange resin treatment and the electrodialysis is reused as all or part of an oxidation catalyst in the oxidation of a cellulosic material, whereby cellulose nanofibers with significantly high transparency can be obtained.

The reason why the deionization efficiency in the electrodialysis can be improved by subjecting the effluent to the ion exchange resin treatment prior to the electrodialysis is inferred as follows. It is considered that in the effluent, water-soluble anionic oligomers and polymers produced by oxidation of polysaccharides are present as impurities and adhere to the ion exchange membrane in the electrodialysis to thereby decrease the function of the ion exchange membrane. Further, it is considered that calcium ions are deposited on a surface of the ion exchange membrane or precipitated in the membrane as scale such as calcium carbonate and calcium sulfate to thereby decrease electric current efficiency. It is considered that by removing the anionic polymers and calcium ions prior to the electrodialysis, a decrease in the function of the ion exchange membrane and a decrease in the electric current efficiency in the electrodialysis can be prevented.

A method for the ion exchange resin treatment of the effluent is not particularly limited. Examples include a method in which the effluent is passed through a column filled with an ion exchange resin.

Ion exchange resins include an anion exchange resin and a cation exchange resin. In the present invention, one of an anion exchange resin and a cation exchange resin may be used, or both an anion exchange resin and a cation exchange resin may be used, but it is preferable to use both an anion exchange resin and a cation exchange resin.

In the case of using both an anion exchange resin and a cation exchange resin, the effluent may be brought into contact with the resins sequentially or with a mixed bed containing both resins, but it is preferable to bring the effluent into contact with the resins sequentially.

(Anion Exchange Resin Treatment)

Examples of an anion exchange resin that can be used in the ion exchange resin treatment include, but are not limited to, various strongly-basic anion exchange resins in which quaternary ammonium groups are introduced as ion exchange groups in a styrene based resin such as crosslinked polystyrene or an acrylic resin as a macromolecular substrate, and various weakly-basic anion exchange resins in which primary to tertiary amines are introduced as ion exchange groups. For example, a commercially-available AMBERLITE IRA958C1 (Rohm and Haas) can be used.

By conducting the anion exchange resin treatment, water-soluble anionic organic substances in the effluent can be removed, whereby the deionization efficiency of the electrodialysis can be improved. By the anion exchange resin treatment of the present invention, for example, 85% or more, preferably 95% or more of water-soluble anionic organic substances in the effluent can be removed.

(Cation Exchange Resin Treatment)

Examples of a cation exchange resin that can be used in the ion exchange resin treatment include, but are not limited to, various strongly-acidic cation exchange resins in which sulfonic acid groups are introduced as ion exchange groups in a styrene based resin such as crosslinked polystyrene, acryl based resin or methacryl based resin as a macromolecular substrate, and various weakly-acidic cation exchange resins in which phosphonic groups, carboxyl groups or the like are introduced as ion exchange groups. For example, a commercially-available AMBERLITE IRC747 (Rohm and Haas) can be used.

By conducting the cation exchange resin treatment, polyvalent cations such as calcium ions in the effluent can be removed, whereby the deionization efficiency of the electrodialysis can be improved. By the cation exchange resin treatment of the present invention, for example, 90% or more, preferably 95% or more of calcium ions in the effluent can be removed.

(Reduction Treatment)

In the present invention, the effluent may be subjected to reduction treatment prior to the electrodialysis of the effluent. The reduction treatment is a treatment for inactivating the oxidative capacity of the oxidizing agent which remains in the effluent after the oxidation reaction of the cellulosic material is completed. Specifically, for example, a reducing agent such as sulfite and thiosulfate is added to the effluent to thereby reduce the concentration of residual halogens (e.g., chlorine) derived from the oxidizing agent in the effluent. By the reduction treatment of the present invention, the concentration of residual halogens (e.g., chlorine) can be reduced to 1 ppm or below. The amount of the reducing agent added is set as appropriate according to the amount of the residual oxidizing agent in the effluent to be treated. In general, the amount is 0.2 g or smaller with respect to 500 ml of the effluent.

By conducting the reduction treatment of the effluent, degradation of the ion exchange resin or membrane can be prevented. In the case of conducting the ion exchange resin treatment prior to the electrodialysis, it is preferable to conduct the reduction treatment prior to the ion exchange resin treatment.

(Production of Cellulose Nanofibers from Oxidized Pulp)

Oxidized pulp obtained by the oxidation of the cellulosic material is defibrated and dispersed by wet mechanical disintegration treatment, whereby cellulose nanofibers which are cellulose single microfibrils with a width of about 2 to 5 nm and a length of about 1 to 5 μm can be obtained. In the wet mechanical disintegration treatment, a mixer, a stirrer, an emulsifier, and a disperser, such as a high-speed shear mixer, a high pressure homogenizer and an ultrahigh pressure homogenizer, can be used singly or in combination of two or more, as necessary.

Further, oxidized pulp which is produced using the effluent of the present invention obtained by the deionization to an inorganic salt concentration of less than 0.4% is defibrated/dispersed, whereby a cellulose nanofiber dispersion with high transparency can be obtained. The transparency of the cellulose nanofiber dispersion obtained by the method of the present invention is preferably 75% or higher, more preferably 80% or higher, even more preferably 90% or higher, in terms of the transmittance of light with 660 nm wavelength in a 0.1% (w/v) aqueous dispersion.

EXAMPLES

The present invention is described in detail by the following Examples. However, it is understood that the scope of the present invention is not limited by the Examples.

(Oxidation of Cellulosic Material)

Five grams (absolute dry weight) of bleached, unbeaten sulfite pulp derived from coniferous tree (Nippon Paper Chemicals Corporation) was added to 500 ml of an aqueous solution in which 78 mg (0.5 mmol) of 2,2,6,6-tetramethyl-1-piperidin-N-oxyradical (TEMPO) and 754 mg (7 mmol) of sodium bromide were dissolved, and the mixture was stirred until the pulp was evenly dispersed. After 12.5 ml (2 mol/L) of an aqueous solution of sodium hypochlorite was added to the reaction system, the pH was adjusted to pH 10.3 with an aqueous solution of 0.5 N hydrochloric acid, and oxidation reaction was initiated. During the reaction, the pH of the system decreased, so an aqueous solution of 0.5 N sodium hydroxide was added successively to adjust the pH to pH 10 while the reaction was conducted for 2 hours. The resulting oxidized pulp was separated by filtration with a glass filter, and the resulting filtrate was used as an effluent containing TEMPO in the Examples below.

The amount of carboxyl groups of the oxidized pulp obtained above was 1.55 mmol/g, as measured by the method described below. Further, the oxidized pulp was defibrated/dispersed by a high shear mixer equipped with a rotary blade (peripheral speed 37 m/s, Nihonseiki Kaisha Ltd.), whereby a cellulose nanofiber dispersion was prepared. The transparency (transmittance of 660-nm light) of 0.1% (w/v) cellulose nanofiber dispersion thus obtained was 97.0%. These results are shown in Table 2 as Reference Example 1.

(Quantitative Determination of TEMPO Contained in Effluent)

A TN (total nitrogen) unit was built into a TOC-V analyzer (Shimadzu Corporation), and TN (total nitrogen concentration, mg/L) in the effluent containing TEMPO was measured. Further, solutions in which TEMPO was dissolved in ultrapure water at different concentrations were prepared, and TN of each of the solutions was measured. Then, a calibration curve showing the relation between TN and TEMPO concentrations was prepared. The TEMPO concentration (mg/L) was calculated from TN (mg/L) of each effluent using the calibration curve.

Further, from the TEMPO concentration of the effluent obtained by the oxidation of the cellulosic material and the TEMPO concentration of the effluent after the electrodialysis, the TEMPO recovery rate after the deionization treatment was calculated.

(Measurement of Inorganic Salt Concentration of Effluent)

The inorganic salt concentration of the effluent obtained by the oxidation of the cellulosic material and the inorganic salt concentration of the effluent after the electrodialysis were measured with a conductivity meter (DKK-TOA Corporation, CT-57101B). Using these measured values, the deionization rate was calculated.

(Measurement of Amount of Carboxyl Groups of Oxidized Pulp)

Sixty milliliters of 0.5% by mass slurry of oxidized pulp was prepared, and an aqueous solution of 0.1 M hydrochloric acid was added to give a pH of 2.5. Then, an aqueous solution of 0.05 N sodium hydroxide was dropped, and the conductivity was measured until the pH reached pH 11. From the amount of sodium hydroxide (a) consumed during a weakly acidic neutralization phase in which a change in the conductivity was gradual, the amount of carboxyl groups of the oxidized pulp was calculated by the following formula:

Amount of carboxyl groups [mmol/g pulp]=a [ml]× 0.05/mass of oxidized pulp [g].

(Measurement of Transparency of Cellulose Nanofiber Dispersion)

The transparency of 0.1% (w/v) cellulose nanofiber dispersion was measured with a UV-VIS spectrophotometer UV-265FS (Shimadzu Corporation) as a transmittance of 660-nm light.

(Quantitative Determination of Residual Chlorine Contained in Effluent)

The amount of residual chlorine in the effluent was measured with a portable high concentration residual chlorine analyzer (HI 95734) (Hanna Instruments Japan).

(Quantitative Determination of Water-Soluble Organic Substances Contained in Effluent)

The amount of water-soluble organic substances contained in the effluent was measured with a total organic carbon analyzer (TOC-V) (Shimadzu Corporation) as a total organic carbon (TOC).

(Quantitative Determination of Calcium Ions Contained in Effluent)

The amount of calcium ions contained in the effluent was measured with an ICP emission spectrophotometer (Vista-MPX) (Seiko Instruments Inc.).

Example 1

The above effluent in an amount of 500 ml was deionized by a desktop deionizer MICRO ACILYZER S3 Electrodialyzer (ASTOM Corporation, standard deionization capacity: 500 ml/Hr). The membrane used was a cartridge type ion exchange membrane NEOSEPTA Cartridge AC-220-550 (ASTOM Corporation, effective current-carrying area 550 $cm^2$, anion and cation exchange type, molecular weight cut-off: 300). The treatment temperature was room temperature (22° C.). As an electrode solution, 500 g of an aqueous solution of 0.28 N sodium sulfate was used. As a liquid for recovering salts, 500 g of ultrapure water was used. A voltage of 9.0 V was applied, and electrodialysis was conducted for 10 minutes, with a terminal current set to 0 A; as a result, the electric current which was 0 A at the beginning was 0.61 A at the end. The conductivity was 6.1 mS/cm at the beginning of the electrodialysis and 2.6 mS/cm at the end of the electrodialysis. The TEMPO recovery rate after the deionization treatment was 97.2%. The deionization rate calculated from the conductivity was 57%, and the inorganic salt concentration was 0.19%.

Example 2

Except that the electrodialysis time was 15 minutes, the procedure of Example 1 was repeated. The electric current which was 0 A at the beginning was 0.29 A at the end. The conductivity was 6.1 mS/cm at the beginning of the electrodialysis and 0.7 mS/cm at the end of the electrodialysis. The TEMPO recovery rate after the deionization treatment was 93.9%. The deionization rate calculated from the conductivity was 89%, and the inorganic salt concentration was 0.05%.

Example 3

Except that the electrodialysis time was 20 minutes, the procedure of Example 1 was repeated. The electric current which was 0 A at the beginning was 0 A at the end. The conductivity was 6.1 mS/cm at the beginning of the electrodialysis and 0 mS/cm at the end of the electrodialysis. The TEMPO recovery rate after the deionization treatment was 86.1%. The deionization rate calculated from the conductivity was 100%, and the inorganic salt concentration was 0%.

Comparative Example 1

Except that the electrodialysis time was 3 minutes, the procedure of Example 1 was repeated. The electric current which was 0 A at the beginning was 0.32 A at the end. The conductivity was 6.1 mS/cm at the beginning of the electrodialysis and 5.5 mS/cm at the end of the electrodialysis. The TEMPO recovery rate after the deionization treatment was 99.6%. The deionization rate calculated from the conductivity was 8%, and the inorganic salt concentration was 0.41%.

Example 4

After 754 mg (7 mmol) of sodium bromide was dissolved in the entire effluent in an amount of 500 ml (containing 0.486 mmol of TEMPO) obtained in Example 1, 5 g (absolute dry weight) of bleached, unbeaten sulfite pulp derived from coniferous tree (Nippon Paper Chemicals Corporation; amount of carboxyl groups: 0.003 mmol/g) was mixed and stirred until the pulp was evenly dispersed. After 12.5 ml (25 mmol) of an aqueous solution of 2M sodium hypochlorite was added to the reaction system, the pH was adjusted to pH 10.3 with an aqueous solution of 0.5 N hydrochloric acid, and oxidation reaction was initiated. During the reaction, the pH of the system decreased, so an aqueous solution of 0.5 N sodium hydroxide was added successively to adjust the pH to pH 10 while the reaction was conducted for 2 hours. After the reaction was completed, the pulp was separated by filtration with a glass filter and washed sufficiently with water to obtain oxidized pulp. The amount of carboxyl groups of the oxidized pulp thus obtained was 1.37 mmol/g.

Further, the oxidized pulp was defibrated/dispersed by a high shear mixer equipped with a rotary blade (peripheral speed 37 m/s, Nihonseiki Kaisha Ltd.), whereby 0.1% cellulose nanofiber dispersion was prepared. The transparency (transmittance of 660-nm light) of 0.1% (w/v) cellulose nanofiber dispersion thus obtained was 80.5%.

Example 5

Except that the effluent obtained in Example 2 (containing 0.470 mmol of TEMPO) was used, the procedure of Example 4 was repeated to obtain oxidized pulp. The amount of carboxyl groups of the oxidized pulp thus obtained was 1.33 mmol/g.

Further, from the oxidized pulp thus obtained, a cellulose nanofiber dispersion was obtained by the same procedure as in Example 4. The transparency of 0.1% (w/v) cellulose nanofiber dispersion thus obtained was 79.5%.

Example 6

Except that the effluent obtained in Example 3 (containing 0.431 mmol of TEMPO) was used, the procedure of Example 4 was repeated to obtain oxidized pulp. The amount of carboxyl groups of the oxidized pulp thus obtained was 1.27 mmol/g.

Further, from the oxidized pulp thus obtained, a cellulose nanofiber dispersion was obtained by the same procedure as in Example 4. The transparency of 0.1% (w/v) cellulose nanofiber dispersion thus obtained was 76.1%.

Comparative Example 2

Except that the effluent obtained in Comparative Example 1 (containing 0.498 mmol of TEMPO) was used, the procedure of Example 4 was repeated to obtain oxidized pulp. The amount of carboxyl groups of the oxidized pulp thus obtained was 1.09 mmol/g.

Further, from the oxidized pulp thus obtained, a cellulose nanofiber dispersion was obtained by the same procedure as in Example 4. The transparency of 0.1% (w/v) cellulose nanofiber dispersion thus obtained was 70.6%.

Comparative Example 3

Except that an effluent which had not been subjected to electrodialysis (containing 0.500 mmol of TEMPO; inorganic salt concentration: 0.45%) was used, the procedure of Example 4 was repeated to obtain oxidized pulp. The amount of carboxyl groups of the oxidized pulp thus obtained was 1.00 mmol/g.

Further, from the oxidized pulp thus obtained, a cellulose nanofiber dispersion was obtained by the same procedure as in Example 4. The transparency of 0.1% (w/v) cellulose nanofiber dispersion thus obtained was 62.8%.

Example 7

The amount of residual chlorine in 500 ml of the effluent was measured; the amount was 37 ppm. Thus, 0.031 g of sodium sulfite (reducing agent) was added to thereby adjust the amount of residual chlorine in the effluent to 1 ppm or below (treatment with reducing agent). Then, an aqueous solution of 0.5 N hydrochloric acid was added to adjust the pH to pH 7. Thereafter, the effluent was passed through a column filled with 70 mL of commercially-available anion exchange resin (Rohm and Haas, AMBERLITE IRA958C1); as a result, the TOC was dropped from 750 ppm to 190 ppm (water-soluble organic substance removal rate: 75%). The effluent was then passed through a column filled with 70 mL of commercially-available cation exchange resin (Rohm and Haas, AMBERLITE IRC747); as a result, the calcium ion concentration was dropped from 1.9 ppm to 0.08 ppm (calcium ion removal rate: 95.8%). At the end, the effluent was subjected to electrodialysis using a desktop deionizer MICRO ACILYZER S3 Electrodialyzer (ASTOM Corporation, standard deionization capacity: 500 ml/Hr). The membrane used was a cartridge type ion exchange membrane NEOSEPTA cartridge AC-220-550 (ASTOM Corporation, effective current-carrying area 550 $cm^2$, anion and cation exchange type, molecular weight cutoff: 300). The treatment temperature was 22° C. As an electrode solution, 500 g of an aqueous solution of 0.28 N sodium sulfate was used. As a liquid for recovering salts, 500 g of ultrapure water was used. A voltage of 12.1 V was applied, and electrodialysis was conducted for 10 minutes, with a terminal current set to 0 A. The conductivity was 6.1 mS/cm at the beginning of the electrodialysis and 1.2 mS/cm at the end of the electrodialysis. The TEMPO recovery rate after the deionization treatment was 98.2%. The deionization rate calculated from the conductivity was 80%, and the inorganic salt concentration was 0.10%.

Then, oxidized pulp was produced by the same procedure as in Example 4 using the effluent thus obtained (containing 0.491 mmol of TEMPO). The amount of carboxyl groups of the oxidized pulp thus obtained was 1.46 mmol/g.

Further, from the oxidized pulp thus obtained, a cellulose nanofiber dispersion was obtained by the same procedure as in Example 4. The transparency of 0.1% (w/v) cellulose nanofiber dispersion thus obtained was 95.2%.

Example 8

Except that the electrodialysis time was 15 minutes, the procedure of Example 7 was repeated to deionize the effluent.

Then, oxidized pulp and cellulose nanofiber dispersion were prepared by the same procedure as in Example 7 using the effluent thus obtained (containing 0.481 mmol of TEMPO).

Example 9

Except that the electrodialysis time was 20 minutes, the procedure of Example 7 was repeated to deionize the effluent. Then, oxidized pulp and cellulose nanofiber dispersion were prepared by the same procedure as in Example 7 using the effluent thus obtained (containing 0.471 mmol of TEMPO).

Example 10

Except that no cation exchange resin treatment was conducted, the procedure of Example 7 was repeated to deionize the effluent. Then, oxidized pulp and cellulose nanofiber dispersion were prepared by the same procedure as in Example 7 using the effluent thus obtained (containing 0.490 mmol of TEMPO).

Example 11

Except that no anion exchange resin treatment was conducted, the procedure of Example 7 was repeated to deionize the effluent. Then, oxidized pulp and cellulose nanofiber dispersion were prepared by the same procedure as in Example 7 using the effluent thus obtained (containing 0.487 mmol of TEMPO).

Example 12

Except that neither anion exchange resin treatment nor cation exchange resin treatment was conducted, the procedure of Example 7 was repeated to deionize the effluent. Then, oxidized pulp and cellulose nanofiber dispersion were prepared by the same procedure as in Example 7 using the effluent thus obtained (containing 0.486 mmol of TEMPO).

Example 13

Except that the electrodialysis time was 3 minutes, the procedure of Example 7 was repeated to deionize the effluent. Then, oxidized pulp and cellulose nanofiber dispersion were prepared by the same procedure as in Example 7 using the effluent thus obtained (containing 0.499 mmol of TEMPO).

The deionization rate, the inorganic salt concentration after the deionization, and the TEMPO recovery rate of the effluents which were subjected to the electrodialysis in accordance with Examples 1 to 3 and 7 to 13 and Comparative Example 1 are shown in Table 1. The amount of carboxy groups of oxidized pulp and the transparency of cellulose nanofiber dispersion prepared in accordance with Examples 4 to 13 and Comparative Examples 2 and 3 are shown in Table 2.

TABLE 1

| | | Ion exchange resin | | Electrodialysis | | | Deionization rate (%) | Inorganic salt concentration after deionization (%) | TEMPO recovery rate (%) |
| | Reducing agent | Anion exchange | Cation exchange | Time (min) | Conductivity Beginning (mS/cm) | End (mS/cm) | | | |
|---|---|---|---|---|---|---|---|---|---|
| Example 1 | — | — | — | 10 | 6.1 | 2.6 | 57 | 0.19 | 97.2 |
| Example 2 | — | — | — | 15 | 6.1 | 0.7 | 89 | 0.05 | 93.9 |
| Example 3 | — | — | — | 20 | 6.1 | 0 | 100 | 0 | 86.1 |
| Example 7 | Used | Used | Used | 10 | 6.1 | 1.2 | 80 | 0.10 | 98.2 |
| Example 8 | Used | Used | Used | 15 | 6.1 | 0.3 | 95 | 0.03 | 96.2 |
| Example 9 | Used | Used | Used | 20 | 6.1 | 0 | 100 | 0 | 94.2 |
| Example 10 | Used | Used | — | 10 | 6.1 | 1.6 | 74 | 0.12 | 98.0 |
| Example 11 | Used | — | Used | 10 | 6.1 | 2.3 | 63 | 0.17 | 97.4 |
| Example 12 | Used | — | — | 10 | 6.1 | 2.6 | 57 | 0.19 | 97.2 |
| Example 13 | Used | Used | Used | 3 | 6.1 | 4.9 | 20 | 0.35 | 99.8 |
| Comparative Example 1 | — | — | — | 3 | 6.1 | 5.5 | 8 | 0.41 | 99.6 |

*The inorganic salt concentration of effluent before deionization was 0.45%.

TABLE 2

| | Effluent containing catalyst used in production of oxidized pulp | Amount of carboxyl groups of oxidized pulp (mmol/g) | Transparency of cellulose nanofiber dispersion (%) |
|---|---|---|---|
| Example 4 | Effluent of Example 1 after electrodialysis | 1.37 | 80.5 |
| Example 5 | Effluent of Example 2 after electrodialysis | 1.33 | 79.5 |
| Example 6 | Effluent of Example 3 after electrodialysis | 1.27 | 76.1 |
| Example 7 | Effluent of Example 7 after electrodialysis | 1.46 | 95.2 |
| Example 8 | Effluent of Example 8 after electrodialysis | 1.48 | 95.8 |
| Example 9 | Effluent of Example 9 after electrodialysis | 1.50 | 96.4 |
| Example 10 | Effluent of Example 10 after electrodialysis | 1.44 | 90.1 |

TABLE 2-continued

|  | Effluent containing catalyst used in production of oxidized pulp | Amount of carboxyl groups of oxidized pulp (mmol/g) | Transparency of cellulose nanofiber dispersion (%) |
|---|---|---|---|
| Example 11 | Effluent of Example 11 after electrodialysis | 1.39 | 82.8 |
| Example 12 | Effluent of Example 12 after electrodialysis | 1.37 | 80.5 |
| Example 13 | Effluent of Example 13 after electrodialysis | 1.15 | 75.1 |
| Comparative Example 2 | Effluent of Comparative Example 1 after electrodialysis | 1.09 | 70.6 |
| Comparative Example 3 | Effluent which was not subjected to electrodialysis | 1.00 | 62.8 |
| Reference Example 1 | — | 1.55 | 97.0 |

From the results shown in Table 1 it is understood that by conducting electrodialysis of an effluent, TEMPO can be recovered at a high recovery rate while deionizing the effluent.

From the results shown in Table 2 it is understood that when an effluent which was subjected to electrodialysis in accordance with the method of the present invention is reused in oxidation of a cellulosic material, a sufficient amount of carboxyl groups can be introduced into the cellulosic material. This shows that a catalyst (TEMPO) in the effluent possesses adequate oxidative capacity even after the electrodialysis.

It is also understood that by defibrating and dispersing the oxidized pulp thus obtained, a cellulose nanofiber dispersion with high transparency can be produced.

The invention claimed is:

1. A method of recovering an N-oxyl compound from an effluent which is produced in oxidation of a cellulosic material with an oxidizing agent in the presence of (1) an N-oxyl compound and (2) a compound selected from the group consisting of a bromide, an iodide and a mixture thereof, comprising subjecting the effluent to deionization by electrodialysis such that the resulting effluent has an inorganic salt concentration of less than 0.4% wherein the effluent to be subjected to the deionization is produced by removing an oxidized cellulosic material after completion of the oxidation reaction of the cellulosic material, and wherein the effluent to be subjected to the deionization comprises the N-oxyl compound.

2. The method of claim 1, wherein the effluent is subjected to ion exchange resin treatment prior to the deionization by electrodialysis.

3. The method of claim 1, wherein the effluent is subjected to reduction treatment prior to the deionization by electrodialysis.

4. The method of claim 1, wherein the effluent is subjected to reduction treatment and then ion exchange resin treatment and thereafter deionization by electrodialysis.

5. The method of claim 1, wherein the N-oxyl compound which is recovered is 2,2,6,6-tetramethyl-1-piperidin-N-oxyradical (TEMPO), 4-hydroxy-2,2,6,6-tetramethyl-1-piperidin-N-oxyradical (4-hydroxy TEMPO), a 4-hydroxy TEMPO derivative obtained by etherification or esterification of a hydroxyl group of 4-hydroxy TEMPO, an aza-adamantane type nitroxy radical, or a mixture thereof.

* * * * *